United States Patent
Suh et al.

(10) Patent No.: US 9,528,112 B2
(45) Date of Patent: Dec. 27, 2016

(54) COMPOSITION COMPRISING MATERIAL FOR INHIBITING SCF OR RECEPTOR THEREOF FOR TREATING OR PREVENTING DISEASES ASSOCIATED WITH VASCULAR PERMEABILITY

(71) Applicant: AJOU UNIVERSITY INDUSTRY-ACADEMIC COOPERATION FOUNDATION, Gyeonggi-do (KR)

(72) Inventors: Won Hee Suh, Gyeonggi-do (KR); Ji Yeon Kim, Seoul (KR)

(73) Assignee: AJOU UNIVERSITY INDUSTRY-ACADEMIC COOPERATION FOUNDATION (KR)

( * ) Notice: Subject to any disclaimer, the term of this patent is extended or adjusted under 35 U.S.C. 154(b) by 0 days.

(21) Appl. No.: 14/398,531

(22) PCT Filed: Oct. 25, 2012

(86) PCT No.: PCT/KR2012/008794
§ 371 (c)(1),
(2) Date: Nov. 3, 2014

(87) PCT Pub. No.: WO2013/165061
PCT Pub. Date: Nov. 7, 2013

(65) Prior Publication Data
US 2015/0191729 A1 Jul. 9, 2015

(30) Foreign Application Priority Data
May 4, 2012 (KR) ........................ 10-2012-0047750

(51) Int. Cl.
*A61K 38/18* (2006.01)
*A61K 38/17* (2006.01)
*A61K 31/713* (2006.01)
*G01N 33/68* (2006.01)
*C12N 15/115* (2010.01)
*C07K 16/28* (2006.01)
*C07K 16/24* (2006.01)
*C12N 15/113* (2010.01)
*A61K 39/00* (2006.01)

(52) U.S. Cl.
CPC ........... *C12N 15/115* (2013.01); *A61K 31/713* (2013.01); *A61K 38/17* (2013.01); *A61K 38/18* (2013.01); *C07K 16/24* (2013.01); *C07K 16/28* (2013.01); *C07K 16/2803* (2013.01); *C12N 15/113* (2013.01); *C12N 15/1138* (2013.01); *G01N 33/6863* (2013.01); *A61K 2039/505* (2013.01); *C07K 2317/76* (2013.01); *C12N 15/1136* (2013.01); *C12N 2310/11* (2013.01); *C12N 2310/14* (2013.01); *C12N 2310/16* (2013.01); *G01N 2333/52* (2013.01); *G01N 2333/715* (2013.01); *G01N 2500/02* (2013.01); *G01N 2500/10* (2013.01); *G01N 2800/7057* (2013.01)

(58) Field of Classification Search
CPC .............. C12N 15/1138; C12N 15/113; C12N 15/1136; C12N 15/115; C12N 2310/11; C12N 2310/14; C12N 2310/16; A61K 2039/505; A61K 31/713; A61K 38/17; A61K 38/18; C07K 16/24; C07K 16/28; C07K 2317/76; C07K 16/2803; G01N 2333/52; G01N 2333/715; G01N 2500/02; G01N 33/6863; G01N 2800/7057
See application file for complete search history.

(56) References Cited

U.S. PATENT DOCUMENTS

| 5,989,849 A | * | 11/1999 | Gewirtz | ................. | C07K 14/82 435/29 |
| 6,248,326 B1 | * | 6/2001 | Blair | .................... | C07K 14/475 424/130.1 |
| 2003/0103937 A1 | * | 6/2003 | Besmer | ................ | A61K 38/193 424/85.2 |

(Continued)

OTHER PUBLICATIONS

Search Report from International Application No. PCT/KR2012/008794 (mailed Mar. 29, 2013).
Kirkpatrick et al., "Physiology and cell biology of the endothelium: a dynamic interface for cell communication", *Int J. Microcirc Clin Exp.*, 17(5): p. 231-240 (1997).
Rizwan Siddiwui et al., "Caveolin-1-eNOS signaling promotes p190RhoGAP-A nitration and endothelial permeability", *J. J. Cell Biol.*, 193(5): p. 841-860 (2011).
Aiello et al., "Vascular Endothelial Growth Factor in Ocular Fluid of Patients with Diabetic Retinopathy and Other Retinal Disorders", *The New England Journal of Medicine*, 331(22): p. 1480-1487 (1994).

(Continued)

*Primary Examiner* — Daniel C Gamett
(74) *Attorney, Agent, or Firm* — Merchant & Gould P.C.

(57) ABSTRACT

The present invention relates to a composition comprising a material for inhibiting stem cell factor (SCF) or the receptor thereof for treating or preventing vascular permeability related diseases. Also, the present invention relates to a method for screening for an agent for treating vascular permeability related diseases, comprising the steps of: (a) treating a sample from a patient suspected of having a disease associated with vascular permeability with a candidate material; and (b) comparing the level of expression of the SCF or the receptor thereof with that of a control group. The present invention verifies SCF as a novel target for regulating vascular permeability. When the present invention is used, vascular permeability is decreased in diseases of the eye involving increased vascular permeability, thereby effectively treating or preventing vascular permeability related diseases. Also, vascular permeability can be effectively regulated using the composition. Further, the present invention can be provided as an effective means for screening an agent for treating vascular permeability related diseases by measuring the regulation of the expressions of SCF and c-Kit.

10 Claims, 5 Drawing Sheets

(56) References Cited

U.S. PATENT DOCUMENTS

| | | | | |
|---|---|---|---|---|
| 2003/0194405 A1* | 10/2003 | Takeuchi | ............... | C07K 16/22 424/152.1 |
| 2006/0286117 A1* | 12/2006 | Fine | ....................... | C07K 14/52 424/185.1 |
| 2007/0253951 A1* | 11/2007 | Ng | ......................... | C07K 16/28 424/133.1 |
| 2007/0258952 A1* | 11/2007 | Tong | ........................ | C12N 7/00 424/93.2 |
| 2012/0321629 A1* | 12/2012 | Lukacs | .................. | C07K 16/22 424/139.1 |

OTHER PUBLICATIONS

Kim et al., "Direct and differential effects of stem cell factor on the neovascularization activity of endothelial progenitor cells", *Cardiovascular Research*, 92: p. 132-140 (2011).

El-Asrar et al., "Expression of stem cell factor/c-kit signaling pathway components in diabetic fibrovascular epiretinal membranes", *Molecular Vision*, 16: p. 1098-1107 (2010).

Lim et al., "Stem cell factor/c-Kit signaling in in vitro cultures supports early mouse embryonic development by accelerating proliferation via a mechanism involving *Akt*-downstream genes",*J Assist Reprod Genet*, 27: p. 619-627 (2010).

Ferrera, "Role of Vascular endothelial growth factor in regulation of physiological angiogenesis", *Am J Phystol Cell Phystol*, 280: p. C1358-C1366 (2001).

Jain, "Normalization of Tumor Vasculature: An Emerging Concept in Antiangiogenic Therapy", *Science*, 307: 58-62 (2005).

Adamis et al., "Increased vascular endothelial growth factor levels in the vitreous of eyes with proliferative diabetic retinopathy", *Am J Opthalmol*, 118(4): 445-450 (1994).

Steinbrook, "The Price of Sight—Ranibizumab, Bevacizumab, and the Treatment of Macular Degeneration", *The New England Journal of Medicine*, 335(14): p. 1409-1412 (2006).

Klagsbrun et al., "Molecular angiogenesis", *Chemistry & Biology*, 6: p. R217-R224 (1999).

Ferrera, "Vascular Endothelial Growth Factor: Basic Science and Clinical Progress", *Endocrine Reviews*, 25(4): p. 581-611 (2004).

Thibeault et al., "S-Nitrosylation of β-Catenin by eNOS-Derived NO Promotes VEGF-Induced Endothelial Cell Permeability", *Molecular Cell*, 39: p. 468-476 (2010).

Chiara Gerhardinger et al., "Expression of Vascular Endothelial Growth Factor in the Human Retina and in Nonproliferative Diabetic Retinopathy," American Journal of Pathology, Jun. 1998, vol. 152, No. 6, pp. 1453-1462.

Malika Oubaha and Jean-Philippe Gratton, "Phosphorylation of endothelial nitric oxide synthase by atypical PKCζ contributes to angiopoietin-1-dependent inhibition of VEGF-induced endothelial permeability in vitro," Blood, Vascular Biology, Oct. 8, 2009, vol. 114, No. 15, pp. 3343-3351.

Masahiro Murakami et al., "The FGF system has a key role in regulating vascular integrity," The Journal of Clinical Investigation, Oct. 2008, vol. 118, No. 10, pp. 3355-3366.

Anna A. Birukova et al., "Paxillin Is Involved in the Differential Regulation of Endothelial Barrier by HGF and VEGF," American Journal of Respiratory Cell and Molecular Biology, Jan. 2009, vol. 40, No. 1, pp. 99-107.

Per Levéen et al., "Mice deficient for PDGF B show renal, cardiovascular, and hematological abnormalities," Genes and Development, Aug. 15, 1994, vol. 8, No. 16, pp. 1875-1887.

Philippe Soriano, "Abnormal kidney development and hematological disorders in PDGF β-receptor mutant mice," Genes and Development, Aug. 15, 1994, vol. 8, No. 16, pp. 1888-1896.

William S. Wright and Norman R. Harris, "Ozagrel attenuates early streptozotocin-induced constriction of arterioles in the mouse retina," Experimental Eye Research, Mar. 2008, vol. 86, Issue 3, pp. 528-536.

Zhongli Wang et al., "Attenuation of streptozotocin-induced microvascular changes in the mouse retina with the endothelin receptor A antagonist atrasentan," Experimental Eye Research, Nov. 2010, vol. 91, Issue 5, pp. 670-675.

Leigh Coultas et al., "Endothelial cells and VEGF in vascular development," Nature, Dec. 15, 2005, vol. 438, No. 7070, pp. 937-945.

Peter Besmer et al., "The kit-ligand (steel factor) and its receptor c-kit/W: pleiotropic roles in gametogenesis and melanogenesis," Development, Dec. 1, 1993, vol. 119, Issue Supplement, pp. 125-137.

Alastair D. Reith et al., "W mutant mice with mild or severe developmental defects contain distinct point mutations in the kinase domain of the c-kit receptor," Genes and Development, Mar. 1, 1990, vol. 4, No. 3, pp. 390-400.

Eli Keshet et al., "Embryonic RNA expression patterns of the c-kit receptor and its cognate ligand suggest multiple functional roles in mouse development," The EMBO Journal, 1991, vol. 10, No. 9, pp. 2425-2435.

Table 1, Supplementary Information, From the following article: Leigh Coultas et al., "Endothelial cells and VEGF in vascular development," Nature, Dec. 15, 2005, vol. 438, No. 7070, pp. 937-945.

\* cited by examiner

SEQUENCE LISTING

```
<160> NUMBER OF SEQ ID NOS: 9

<210> SEQ ID NO 1
<211> LENGTH: 21
<212> TYPE: RNA
<213> ORGANISM: Artificial Sequence
<220> FEATURE:
<223> OTHER INFORMATION: control siRNA

<400> SEQUENCE: 1
aauggaagac cacucccacu c                                                21

<210> SEQ ID NO 2
<211> LENGTH: 19
<212> TYPE: RNA
<213> ORGANISM: Artificial Sequence
<220> FEATURE:
<223> OTHER INFORMATION: C-Kit siRNA

<400> SEQUENCE: 2
ucauucuuga ugucucugg                                                   19

<210> SEQ ID NO 3
<211> LENGTH: 19
<212> TYPE: RNA
```

```
<213> ORGANISM: Artificial Sequence
<220> FEATURE:
<223> OTHER INFORMATION: C-Kit siRNA

<400> SEQUENCE: 3
uuugaguuca gacaugagg                                                      19

<210> SEQ ID NO 4
<211> LENGTH: 19
<212> TYPE: RNA
<213> ORGANISM: Artificial Sequence
<220> FEATURE:
<223> OTHER INFORMATION: C-Kit siRNA

<400> SEQUENCE: 4
ucuuauaaag ugcagcuuc                                                      19

<210> SEQ ID NO 5
<211> LENGTH: 19
<212> TYPE: RNA
<213> ORGANISM: Artificial Sequence
<220> FEATURE:
<223> OTHER INFORMATION: C-Kit siRNA

<400> SEQUENCE: 5
uacaaugcca uucugaagc                                                      19

<210> SEQ ID NO 6
<211> LENGTH: 22
<212> TYPE: RNA
<213> ORGANISM: Artificial Sequence
<220> FEATURE:
<223> OTHER INFORMATION: eNOS siRNA

<400> SEQUENCE: 6
accggaacag cacaagaguu au                                                  22

<210> SEQ ID NO 7
<211> LENGTH: 22
<212> TYPE: RNA
<213> ORGANISM: Artificial Sequence
<220> FEATURE:
<223> OTHER INFORMATION: eNOS siRNA

<400> SEQUENCE: 7
agcugcaagg auucagcauu au                                                  22

<210> SEQ ID NO 8
<211> LENGTH: 22
<212> TYPE: RNA
<213> ORGANISM: Artificial Sequence
<220> FEATURE:
<223> OTHER INFORMATION: eNOS siRNA

<400> SEQUENCE: 8
acggaacagc acaagaguua ua                                                  22

<210> SEQ ID NO 9
<211> LENGTH: 22
<212> TYPE: RNA
<213> ORGANISM: Artificial Sequence
```

```
<220> FEATURE:
<223> OTHER INFORMATION: eNOS siRNA

<400> SEQUENCE: 9
ccaggaguau cuuaccugua aa                                           22
```

COMPOSITION COMPRISING MATERIAL FOR INHIBITING SCF OR RECEPTOR THEREOF FOR TREATING OR PREVENTING DISEASES ASSOCIATED WITH VASCULAR PERMEABILITY

This application is a U.S. National Stage Application under 35 U.S.C. §371 of International Patent Application No. PCT/KR2012/008794 filed Oct. 25, 2012, which claims the benefit of priority to Korean Patent Application No. 10-2012-0047750 filed May 4, 2012, the disclosures of all of which are hereby incorporated by reference in their entireties. The International Application was published in Korean on Nov. 7, 2013 as WO 2013/165061. To the extent appropriate, a claim of priority is made to each of the above disclosed applications.

TECHNICAL FIELD

The present invention relates to a composition comprising a material for inhibiting SCF (stem cell factor) or the receptor thereof for treating or preventing vascular permeability related diseases. The present invention also relates to a method for screening an agent for treating vascular permeability related diseases comprising the following steps: (a) treating a sample from a patient suspected of having a disease associated with vascular permeability with a candidate material; and (b) comparing the expression level of SCF or the receptor thereof with that of the control group.

BACKGROUND

The vascular system plays an important role in maintaining normal physiological functions. For example, vascular endothelial cells form the cellular barrier functioning to regulate the migration of fluids, electrolytes, and proteins into tissues and organs. Blood vessels forming such vascular system are the necessary organs for the survival of all body forming cells and for maintaining the normal functions thereof. In particular, the incidence of such diseases that are caused by the lack of blood vessels and the loss of vascular homeostasis is increasing, which makes those diseases as an important target of the treatment.

In relation to the vascular permeability, the factors that cause malfunctioning of the endothelial barrier are complicated and are not yet understood completely, despite studies to maintain and develop the vascular permeability have been widely undergoing (Klagsbrun & Moses, Chemistry & Biology (1999), 6:R217-R224; Ferrara, Endocrine Reviews (2004), 25(4):581-611). The exact mechanism to disturb the vascular permeability has not been clearly explained yet and is only presumed to cooperate closely with other causes of various diseases including cancer, inflammatory disease such as autoimmune disease, and other pathological diseases. It is known that the vascular system related inflammation stimulates the formation of extracellular angiogenesis in relation to the disturbed vascular permeability (Kirkpatrick et al., Int. J. Microcirc. (1997), 17:231-240). For example, up-regulation of the surface adhesion molecules and their ligands, infiltration of inflammatory cells, production of cytokines, release of chemokines, oxidative stress, and activation of innate immunity can cause the vascular system related inflammation. This inflammatory response is typically related to the alteration of the vascular permeability, the transendothelial migration of leucocytes (attachment, migration, and chemotaxis), and the tissue regeneration.

According to the previous reports, angiogenesis and vascular permeability are closely related to hypoxia. In particular, the hypoxia observed in the stage of embryogenesis, the cancer tissues showing active cell proliferation, or the tissues with damaged blood vessels results in breaking a bond between the blood vessel and the endothelial cells to make the permeability unstable. Under this situation, the proliferation and migration of vascular endothelial cells are accelerated to induce angiogenesis. It is also known that various genes expressed differently by the transcription factors such as HIF-1 (hypoxia inducible factor-1) expressed under the hypoxic condition are involved in the mechanism that controls such instability of blood vessels and angiogenesis. Many of those genes are growth factors/cytokines, which are responsible for reducing the cell-cell interaction of vascular endothelial cells to increase the vascular permeability or for promoting the proliferation/migration of vascular endothelial cells to induce angiogenesis.

Abnormal angiogenesis and the regulation of vascular permeability are directly related not only to the formation of organs in the course of embryogenesis but also to many diseases from birth to adulthood. Excessive angiogenesis might cause cancer development, diabetic retinopathy, and rheumatoid arthritis, etc. On the contrary, the lack of angiogenesis causes chronic wound and ischemic cardiovascular disease, etc. The vascular permeability is also related closely to various diseases. Particularly in patients with ischemic brain disease or myocardial infarction, the high vascular permeability results in edema to cause apoptosis of neurons or cardiomyocytes. To establish a fundamental treatment method for such diseases, it is important and urgent to disclose the molecular mechanism that can regulate angiogenesis and vascular permeability. Various attempts have been made to disclose the molecular mechanism responsible for the control of angiogenesis and vascular permeability so far. As a result, it has been confirmed that VEGF (vascular endothelial growth factor) is the representative gene that regulates the vascular permeability and is over-expressed in hypoxia so as to increase the vascular permeability by binding the VEGF-receptor. The VEGF receptor is binding to VE-cadherin that regulates the cell-cell interaction of vascular endothelial cells, so that it can help VEGF to increase the vascular permeability by inducing endocytosis of VE-cadherin. Also, NO generated by VEGF/eNOS induces S-nitrosylation of β-catenin to promote the separation of VE-cadherin therefrom, resulting in the increase of vascular endothelial cell permeability (M. Rizwan et al., J. Cell Bol. (2011)193; 841-850). Thrombin, increasing vascular endothelial cell permeability, induces the generation of NO from eNOS and the activation of RhoA, which results in instability of the actin cytoskeleton and the adherent junction molecules, indicating the increase of vascular permeability (Thibeault et al., Molecular cell (2010) 39; 468-476). So, an attempt has been made to treat diabetic retinopathy caused by the increased vascular permeability by inhibiting VEGF or VEGF receptor. This attempt can also be applied to treat choroidal neovascularization, ROP (retinopathy of prematurity), and age-related macular degeneration caused by angiogenesis of immature blood vessels with high permeability (Aiello, New England Journal of Medicine (1994) 331(22):1480-1487; Adamis, American journal of Ophthalmology (1994) 118:445-450; Steinbrook, New England Journal of Medicine (2006) 355(14):1409-1412; Ferrara, American Journal of Physiol Cell Physiol (2001) 280(6): C1358-C1366). The treatment method based on the inhibition of VEGF or VEGF receptor can induce the normalization of high permeability blood vessels generated in and around a tumor, so that an anti-cancer agent can be delivered in the center of a tumor to increase the anti-cancer treatment effect (Jain, Science (2005)307 (5706): 58-62).

Unfortunately, most of the studies made so far on the regulation of angiogenesis and vascular permeability are limited to VEGF or VEGF receptors, and are focused on the development of the said gene inhibitors with asking more studies on angiogenesis and the control of vascular permeability.

Under this circumstance, the present inventors tried to screen a substance to treat vascular permeability related diseases in eye diseases. In the course of study, the present inventors confirmed that SCF (stem cell factor) increased the vascular permeability and the inhibition of the expression or phosphorylation of SCF or C-Kit (SCR receptor) reduced the vascular permeability, leading to the completion of this invention.

DISCLOSURE

Technical Problem

It is an object of the present invention to provide a composition for treating or preventing vascular permeability related diseases comprising a material for inhibiting SCF (stem cell factor) or the receptor thereof.

It is another object of the present invention to provide a method for regulating the vascular permeability comprising the step of regulating the expression of SCF or the receptor thereof in vitro by using the said composition.

It is also an object of the present invention to provide a method for screening an agent for treating vascular permeability related diseases comprising the following steps: (a) treating a sample from a patient suspected of having a disease associated with vascular permeability with a candidate material; and (b) comparing the expression level of SCF or the receptor thereof with that of the control group.

Technical Solution

To achieve the above objects, the present invention provides a composition for treating or preventing vascular permeability related diseases comprising a material for inhibiting SCF (stem cell factor) or the receptor thereof. More precisely, the said SCF receptor is C-Kit, and the material inhibiting SCF or the receptor thereof is siRNA, an antisense oligonucleotide, an aptamer, or an antibody specific to the SCF or the receptor thereof. In particular, the material to inhibit the SCF receptor is preferably C-Kit siRNA or a SCF receptor inhibiting antibody.

In the meantime, the vascular permeability related diseases herein is preferably selected from the group consisting of diabetic retinopathy, choroidal neovascularization, glaucoma retinitis pigmentosa, ROP (retinopathy of prematurity), age-related macular degeneration, glaucoma, corneal dystrophy, retinoschises, Stargardt's disease, autosomal dominant druzen, Best's macular dystrophy, cystoid macular edema, ischemic retinopathy, inflammation-induced retinal degenerative disease, X-linked juvenile retinoschisis, Malattia Leventinese (ML), Doyne honeycomb retinal dystrophy, and vascular endothelial cell related inflammatory disease. At this time, the treatment of the disease associated with vascular permeability is preferably performed by inhibiting the vascular endothelial cell permeability.

The present invention also provides a method for regulating the vascular permeability comprising the step of regulating the expression of SCF or the receptor thereof in vitro by using the said composition.

The present invention further provides a method for screening an agent for treating vascular permeability related diseases comprising the following steps: (a) treating a sample from a patient suspected of having a disease associated with vascular permeability with a candidate material; and (b) comparing the expression level of SCF or the receptor thereof with that of the control group. More precisely, the SCF receptor herein is C-Kit, and the step (b) can further comprise the step of comparing the phosphorylation level of C-Kit with that of the control group.

Advantageous Effect

The present invention verifies SCF as a novel target for regulating vascular permeability. When the present invention is used, vascular permeability is decreased in diseases of the eye involving increased vascular permeability, thereby effectively treating or preventing vascular permeability related diseases. Also, vascular permeability can be effectively regulated using the composition. Further, the present invention can be provided as an effective means for screening an agent for treating vascular permeability related diseases by measuring the regulation of the expressions of SCF and c-Kit.

BRIEF DESCRIPTION OF THE DRAWINGS

The application of the preferred embodiments of the present invention is best understood with reference to the accompanying drawings, wherein:

FIG. 2A illustrates the NO generation increased by SCF and FIG. 2B illustrates that the endothelial cell permeability increased by SCF can be inhibited by L-NAME. FIG. 2C illustrates that the expression of VE-cadherin on the vascular endothelial cell surface decreased by SCF and VEGF has been recovered by the inhibition of the eNOS expression and the treatment with L-NAME. FIG. 2D illustrates that the endocytosis of VE-cadherin increased by SCF and VEGF has been reduced by the inhibition of the eNOS expression and the treatment with L-NAME.

FIG. 3A and FIG. 3B illustrate the increase of vascular permeability by SCF. FIG. 3C and FIG. 3D illustrate the decrease of vascular permeability by the SCF receptor inhibiting antibody.

FIG. 4A and FIG. 4B illustrate the increase of vascular permeability by SCF. FIG. 4C and FIG. 4D illustrate the decrease of vascular permeability by the SCF receptor inhibiting antibody.

DETAILED DESCRIPTION

Hereinafter, the present invention is described in detail.

In a preferred embodiment of the present invention, the present invention provides a composition for treating or preventing vascular permeability related diseases comprising a material for inhibiting SCF (stem cell factor) or the receptor thereof.

In this invention, the term "SCF (stem cell factor)" indicates the cytokine binding to C-Kit (CD117), which is also called a kit-ligand or a steel factor and exists as a transmembrane protein in a water-soluble form. It is known that the said SCF promotes hematopoiesis, spermatogenesis, and melanogenesis, but whether SCF can increase vascular permeability or not has not been reported, yet. The present inventors first identified that SCF could increase vascular permeability and the inhibition of SCF or the receptor thereof could be effective in treating vascular permeability related diseases.

Particularly, the present inventors targeted SCF or the receptor thereof for our study and confirmed accordingly that the inhibition of SCF or the receptor thereof was effective in treating vascular permeability related diseases. The inhibition of SCF or the receptor thereof can be achieved not only by inhibiting the expression of SCF or the receptor thereof but also by inhibiting the phosphorylation of SCF or the receptor thereof. The information about SCF sequence can be obtained from the known database, but not always limited thereto. For example it can be NCBI GenBank Accession No. NG_012098, and any SCF sequence that demonstrates at least 80%, 90%, and preferably 95% homology can be hired as long as it shows the activity to increase vascular permeability. The said SCF receptor can also be any one that can increase vascular permeability and preferably C-Kit, but not always limited thereto.

In this invention, the term "C-Kit (CD117)" indicates the protein encoding a human KIT gene, which is also called proto oncogene C-Kit or tyrosine-protein kinase Kit. This C-kit is the cytokine receptor expressed on the hematopoietic stem cell surface, which is a receptor protein binding to SCF. It is known that the variant of this receptor is involved in some cancers. The information about C-Kit sequence can be obtained from the known database, but not always limited thereto. For example it can be NCBI GenBank Accession No. BC071593.1, and any C-Kit sequence that demonstrates at least 80%, 90%, preferably 95%, and more preferably 97% homology can be hired as long as it shows the activity to increase vascular permeability.

Figure 1:
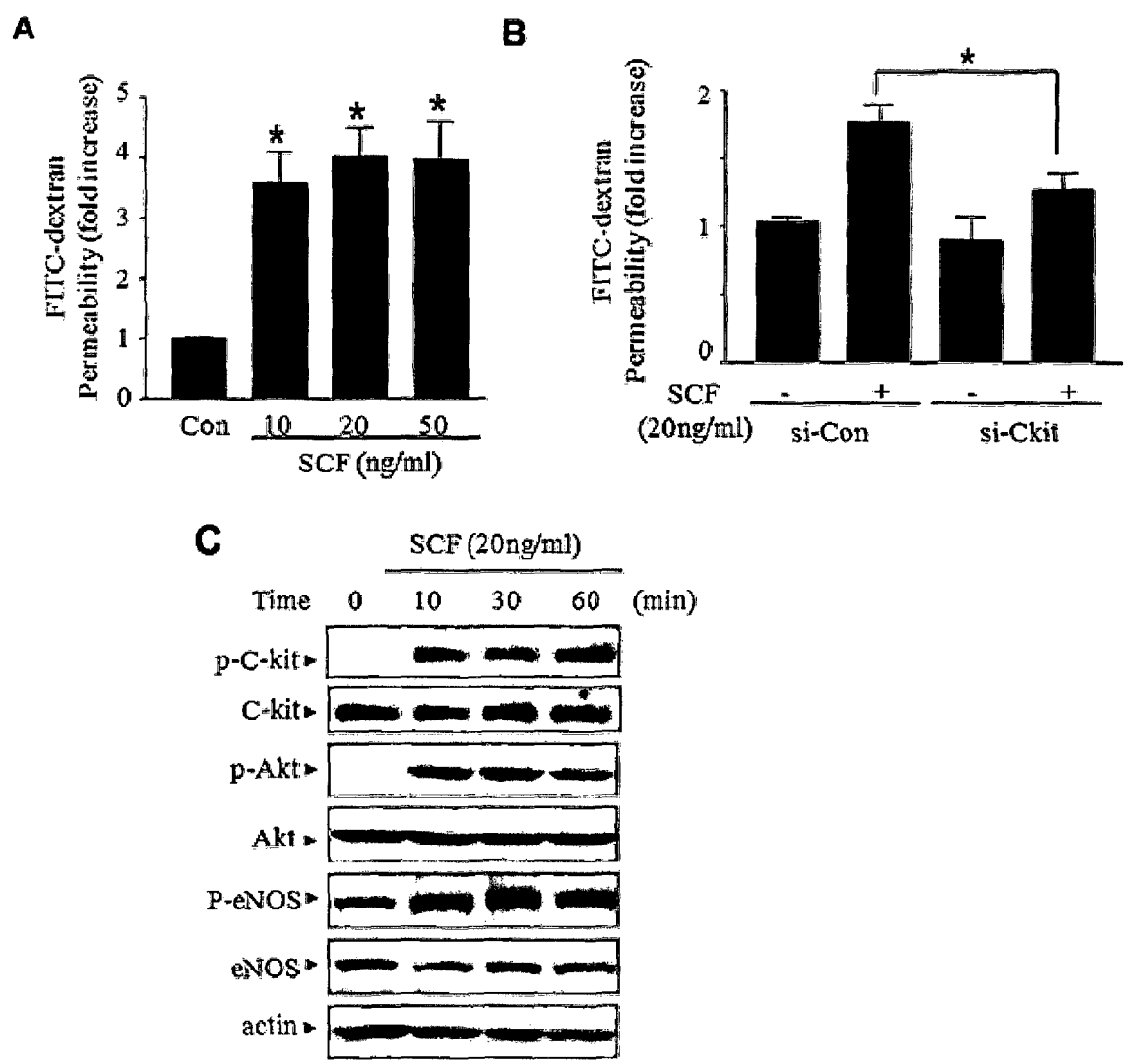
FIG. 1 illustrates the results of analysis, respectively demonstrating the increase of vascular permeability by SCF (A), C-Kit dependence (B), and signaling pathway (C).
Figure 3:
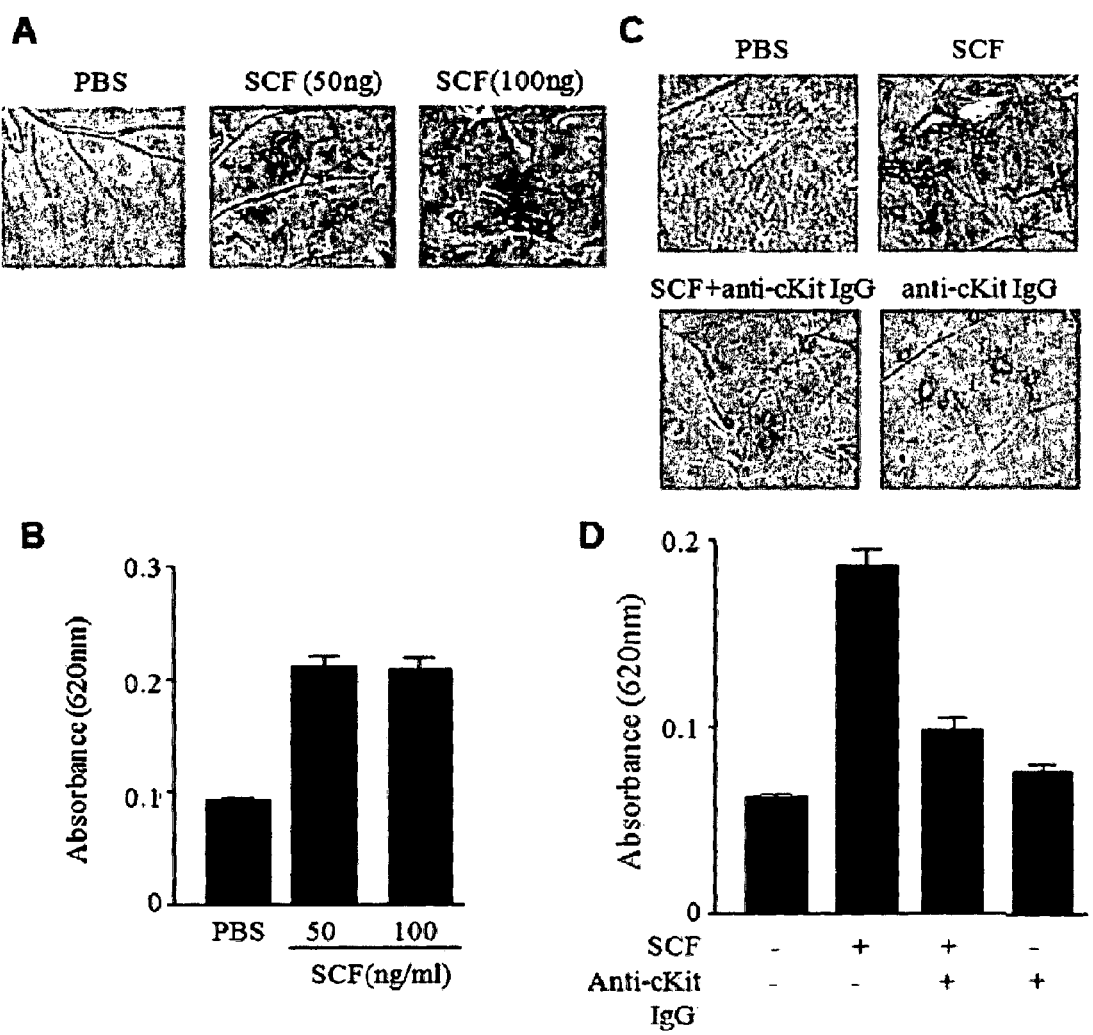
FIG. 3 illustrates the increase of the vascular permeability by SCF, confirmed by the experiment with mouse subcutaneous tissues.
Figure 4:
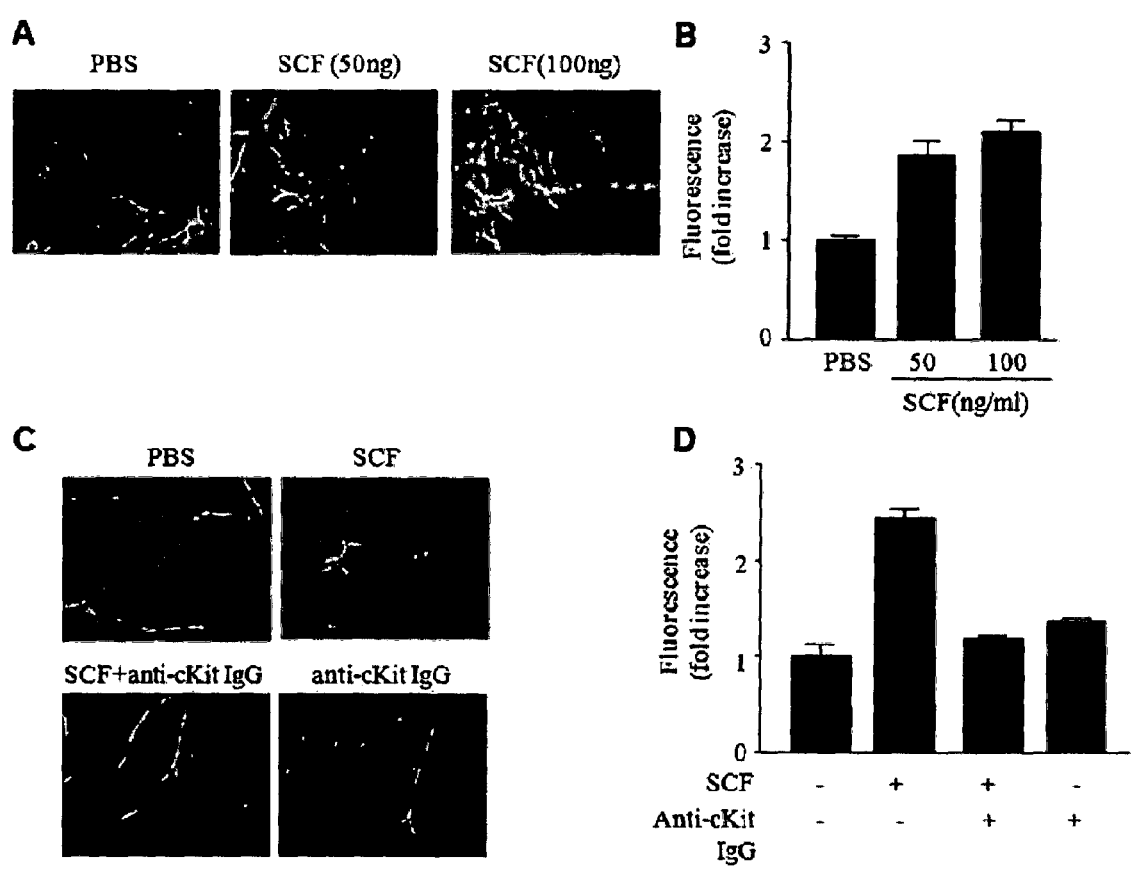
FIG. 4 illustrates the increase of the vascular permeability by SCF, confirmed by the experiment with mouse retinal vessels.
Figure 5:
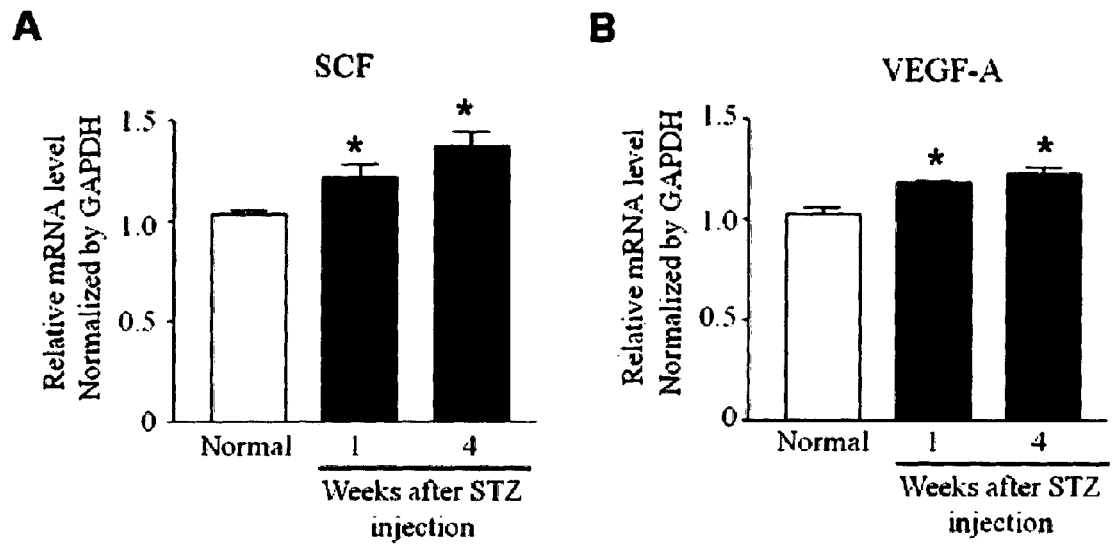
FIG. 5 illustrates the up-regulations of SCF (A) and VEGF (B) in the retina of an animal having diabetic retinopathy.

In a preferred embodiment of the present invention, the present inventors confirmed that the vascular permeability of endothelial cells was increased when the medium in which the vascular endothelial cells were cultured was treated with SCF (FIG. 1A). It was also confirmed that when SCF receptor was inhibited, the vascular permeability was decreased (FIG. 3 and FIG. 4). When the expression of C-Kit, the SCF receptor, was inhibited by siRNA, the vascular permeability was also decreased (FIG. 1B). The expression of SCF was increased in the animal model having diabetic retinopathy, one of the vascular permeability related diseases (FIG. 5).

In this invention, the term "a material inhibiting SCF or the receptor thereof" indicates a material that can inhibit SCF or the receptor thereof, for example C-Kit, that increases vascular permeability, which is functioning to suppress blood-spill by regulating vascular permeability. This material can be used for the purpose of treating or preventing vascular permeability related diseases caused by the increased vascular permeability. This inhibition can be achieved not only by inhibiting the expression of SCF or the receptor thereof but also by inhibiting the phosphorylation of SCF or the receptor thereof.

The material inhibiting SCF or the receptor thereof targets SCF or the receptor thereof to inhibit the expression of SCF or the receptor thereof or the phosphorylation of C-Kit, which is exemplified by a compound, a nucleic acid, a peptide, a virus, or a vector containing the said nucleic acid, etc, but not always limited thereto. In this invention, this material is preferably siRNA, an antisense oligonucleotide, an aptamer, or an antibody specific to SCF or the receptor thereof. The material inhibiting the expression of SCF or the receptor thereof is the one not only inhibiting the expression of SCF or the receptor thereof but also inhibiting the signal transduction induced by SCF or the receptor thereof.

Particularly, when SCF was treated, the phosphorylation of C-kit, the SCF receptor, involved in vascular permeability, was increased and so did the phosphorylation of Akt protein. In addition, the phosphorylation of eNOS related with vascular permeability was increased as well, resulting in the increase of the vascular permeability (FIG. 1C). These results suggest that the vascular permeability can be reduced by inhibiting the phosphorylation of C-Kit based on the suppression of SCF or the phosphorylation of a protein responsible for the signal transduction induced by SCF and C-Kit.

In this invention, the term "siRNA" indicates the nucleic acid molecule that can mediate RNA interference or gene silencing, which can be effectively used for gene knockdown or gene therapy because of its capability of inhibiting the expression of a target gene. The said siRNA is a small RNA fragment in the size of 21~25 nucleotides which is generated by cutting double-stranded RNA with a dicer. This siRNA is specifically binding to mRNA having a corresponding sequence thereto in order to suppress the protein expression. Whether or not the siRNA can induce the complementary mRNA degradation or inhibit the translation thereof can be determined by the complementarity between the siRNA in the size of 21~25 nucleotides and the corresponding mRNA. The material used in this invention to inhibit the transcription of SCF is siRNA. This siRNA is functioning to inhibit the increase of the vascular permeability by suppressing SCF involved in the vascular permeability by taking advantage of the complementarity of the fragment. This siRNA is also functioning to inhibit the vascular permeability by suppressing the expression of C-Kit, the SCF receptor. In a preferred embodiment of the present invention, C-Kit siRNA was used to inhibit the SCF receptor. When the expression of C-Kit was inhibited by using the siRNA confirmed to inhibit C-Kit, the vascular permeability was reduced (FIG. 1B). SCF or C-Kit specific siRNA can be prepared by the conventional method well-known to those in the art with the gene sequence obtained from the informed database. The said C-Kit siRNA is preferably the siRNA having the nucleotide sequence represented by SEQ. ID. NO: 2, NO: 3, NO: 4, or NO: 5, but not always limited thereto.

In this invention, the term "antisense oligonucleotide" indicates DNA, rRNA or the derivatives thereof which contain the complementary sequence to a specific mRNA. The antisense nucleotide is conjugated to the complementary sequence of mRNA to inhibit the translation of mRNA into protein. The sequence of this antisense oligonucleotide is complementary to mRNA of SCF or the receptor thereof and thus the DNA or RNA sequence is linkable to the said mRNA. This can inhibit various essential biological activities including translation, translocation, and maturation of SCF or the receptor thereof. The length of antisense oligonucleotide is 6~100 nucleotides, preferably 8~60 nucleotides, and more preferably 10~40 nucleotides. This antisense oligonucleotide can be synthesized in vitro by the conventional method so as to be delivered into a living body or can be synthesized in vivo. To synthesize antisense oligonucleotide in vitro, RNA polymerase I can be used. To induce the biosynthesis of antisense oligonucleotide in vivo, a vector having the origin of multiple cloning site (MCS) in the opposite direction is used for the transcription of antisense RNA. The antisense RNA is supposed to have a translation stop codon in its sequence so as to prevent the translation of RNA into peptide. The antisense oligonucleotide used in this invention can be designed by referring the nucleotide sequence of SCF or C-Kit according to the conventional method well-known to those in the art.

In this invention, the term "aptamer" indicates a single stranded oligonucleotide, which is a nucleic acid molecule in the size of 20~60 nucleotides and has the binding activity to a small target molecule. This aptamer has a sequence dependent 3-dimensional structure and has the high affinity to a specific material like the antigen antibody response. The said aptamer can be conjugated to a small target molecule to inhibit the activity of the target molecule. The aptamer of the present invention can be RNA, DNA, modified nucleic acid, or the mixture thereof, which is either in the shape of a straight chain or a ring. The aptamer is preferably functioning to inhibit the activity of SCF by binding thereto. It can also bind to C-Kit, the SCF receptor, in order to inhibit the SCF receptor activity, and accordingly it can suppress the binding between SCF and SCF receptor, resulting in the indirect inhibition of SCF activity. The said SCF or C-Kit siRNA can be prepared by the conventional method well-informed to those in the art using the gene sequence obtained from the informed database.

In this invention, the term "antibody" indicates a material that responses to an invaded foreign antigen while it circulates through blood or lymph in the immune system of a living body. This material is also called immunoglobulin since this is one of the globulin proteins generated in the lymphatic tissue. An antibody is a protein generated by B cells. Once it is generated, the antibody is released in the body fluid where it binds to an antigen specifically. An antibody comprises two heavy chains and two light chains. Each of the heavy chains and light chains has a variable region in its N-terminal. Each variable region is composed of three complementarity determining regions (CDRs) and four framework regions (FRs). The complementarity determining regions determine the antigen/antibody binding specificity, and exist as a comparatively short peptide sequence maintained by the framework regions. The antibody herein is preferably an antibody that can inhibit the SCF activity by binding to SCF or the SCF receptor (C-Kit) inhibiting antibody. In a preferred embodiment of the present invention, it was confirmed that the SCF receptor inhibiting antibody was effective in reducing the vascular permeability (FIG. 3 and FIG. 4).

In this invention, the term "L-NAME (L-N-nitro arginine methyl ester)" indicates a nitric oxide synthase (NOS) inhibitor, which plays a role of inhibiting the synthesis of nitric oxide in vascular endothelial cells to regulate the vascular permeability. In a preferred embodiment of the present invention, the said L-NAME was used in order to inhibit the vascular endothelial cell permeability by suppressing NO generated by SCF.

In this invention, the term "blood vessel (or blood vessel system)" indicates the vascular system that carries blood and lymph throughout the whole body, which is more precisely the vessels of the mammalian vascular system including arteries, arterioles, capillaries, venules, veins, and vasa vasorums. In this invention, the term "vascular permeability" indicates the capability of passing through the blood vessels, which is functioning to regulate the blood-spill into the extracellular matrix of the vascular endothelial cells. This vascular permeability includes all the activity to pass through every blood vessel in a living body without a limitation, for example the permeability of vascular endothelial cells is also included.

In a preferred embodiment of the present invention, it was confirmed that when SCF was treated to the vascular endothelial cell culture medium, the vascular permeability of the vascular endothelial cells was increased (FIG. 1A). In addition, it was confirmed that the vascular permeabilities of the mouse subcutaneous tissue (FIGS. 3A and 3B) and the mouse retinal vessels were also increased (FIGS. 4A and 4B).

In this invention, the term "vascular permeability related diseases" indicates the disease caused by the failure of normal vascular permeability regulation. In general, it indicates the disease that accompanies hemorrhage caused by the increased vascular permeability. The vascular permeability related diseases herein is exemplified by diabetic retinopathy, choroidal neovascularization, glaucoma retinitis pigmentosa, ROP (retinopathy of prematurity), age-related macular degeneration, glaucoma, corneal dystrophy, retinoschises, Stargardt's disease, autosomal dominant druzen, Best's macular dystrophy, cystoid macular edema, ischemic retinopathy, inflammation-induced retinal degenerative disease, X-linked juvenile retinoschisis, Malattia Leventinese (ML), Doyne honeycomb retinal dystrophy, and vascular endothelial cell related inflammatory disease, and preferably diabetic retinopathy or age-related macular degeneration, but not always limited thereto.

Figure 6:
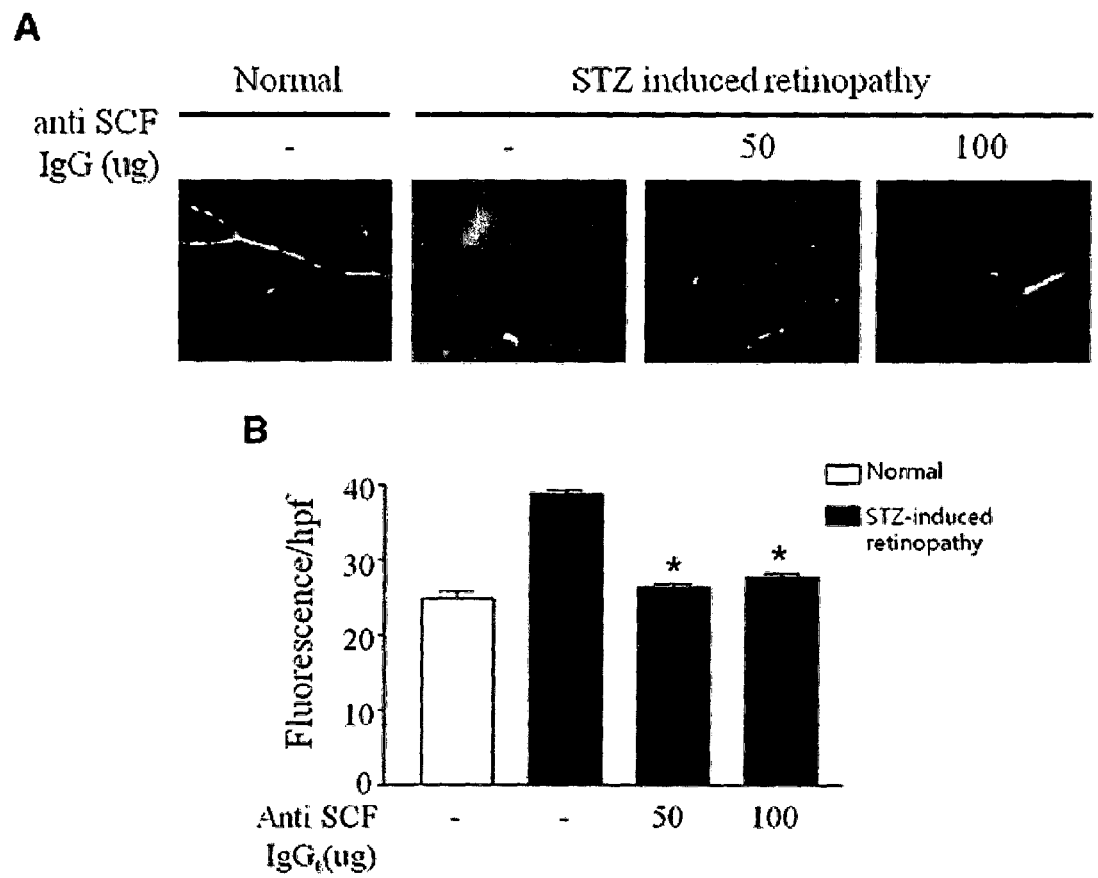
FIG. 6 illustrates the inhibition of the increase of the vascular permeability by the SCF inhibiting antibody in the retina of an animal having diabetic retinopathy.

In a preferred embodiment of the present invention, it was confirmed that the expression of SCF was increased over the time in an animal model having diabetic retinopathy, one of the most representative vascular permeability related diseases (FIG. 5A), suggesting a high possibility for SCF being a target of the prevention or treatment of vascular permeability related diseases. It was also confirmed that the SCF inhibiting antibody worked to reduce the vascular permeability (FIG. 6), suggesting that a material that can inhibit SCF is effective in treating vascular permeability related diseases.

In this invention, the term "treatment" or "treating" indicates a clinical intervention to alter the natural process of a cell or of an individual, the target of treatment. This clinical intervention can be performed during the progress of clinical pathological status or to prevent the status. The treatment effect that we are aiming at and expecting includes preventing the outbreak or recurrence of a disease, alleviating the symptoms, decreasing the direct or indirect pathological results induced by the disease, reducing the progress speed of the disease, relieving the disease status, and improving the prognosis of the disease. All the actions taken to improve the vascular permeability related diseases by administering the composition comprising a material for inhibiting SCF or C-Kit, the SCF receptor, of the present invention to a subject are preferably included in the criteria of "treatment" of the invention.

In this invention, the term "prevention" or "preventing" indicates all the actions to inhibit or delay the vascular permeability related diseases by administering the composition comprising a material for inhibiting SCF or C-Kit, the SCF receptor, of the present invention.

The composition of the present invention can be a pharmaceutical composition to treat vascular permeability related diseases by suppressing the permeability of vascular endothelial cells.

The pharmaceutical composition of the present invention can additionally include generally used carriers, excipients or diluents. The composition containing the pharmaceutically acceptable carrier of the present invention can be prepared for oral or parenteral administration by mixing with generally used diluents or excipients such as fillers, extenders, binders, wetting agents, disintegrating agents and surfactants. Solid formulations for oral administration are tablets, pills, powders, granules and capsules. These solid formulations are prepared by mixing one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, lyophilized preparations and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

The pharmaceutical composition of the present invention can be formulated in a form selected from the group consisting of tablet, pill, powder, granule, capsule, suspension, liquid, emulsion, syrup, sterilized solution, non-soluble solvent, lyophilized preparation, and suppository.

In this invention, the term "vascular endothelial cells" indicate the cells surrounding the endothelium of a blood vessel and play a key role in the formation of a new blood vessel. In particular, the cells regulate the formation of capillaries, the tiniest but most abundant blood vessels in a living body.

In a preferred embodiment of the present invention, the vascular endothelial cells were cultured with different concentrations of SCF. As a result, the permeability of vascular endothelial cells was increased by the treatment of SCF dose-dependently. Particularly, when the vascular endothelial cells were cultured with SCF at different concentrations of 10, 20, and 50 ng/g, the permeability of vascular endothelial cells was increased SCF dose dependently (FIG. 1A). That is, SCF increased the permeability of vascular endothelial cells, which suggests the inhibition of SCF might reduce the vascular permeability.

The present invention also relates to a method for treating vascular permeability related diseases comprising the step of administering a composition comprising SCF or C-Kit, the SCF receptor, to a subject.

In this invention, the term "subject" indicates all the animals including human having the vascular permeability related diseases of the present invention. The vascular permeability related diseases can be alleviated or treated by administering the composition of the present invention to a subject.

In this invention, the term "alleviation" indicates all the actions that can relieve the vascular permeability related diseases or are advantageous for treating the disease by administering the composition of the present invention.

The composition of the present invention is preferably administered to a subject at a pharmaceutically effective dose.

In this invention, the term "administration" indicates the introduction of the pharmaceutical composition of the present invention into a subject via a proper pathway. The administration pathway can be either oral or any other parenteral methods that can deliver the composition to the target tissue.

The pharmaceutical composition of the present invention can be administered to a subject properly by the conventional method, through a proper administration pathway at a proper dose, considering the purpose of use understood by those in the art. The administration pathway herein is exemplified by oral, parenteral, hypodermic, intraperitoneal, intrapulmonary, and intranasal administration. The parenteral administration herein is exemplified by intramuscular injection, intravenous injection, intra-arterial injection, intraperitoneal injection, or hypodermic injection. A proper dose and frequency of the administration can be determined by those in the art according to the informed knowledge in this field. The actual dose and frequency of the pharmaceutical composition of the invention can be determined by the symptoms as treatment targets, administration pathway, gender, health condition, diet, age and weight of a patient, and severity of disease, etc.

In this invention, the term "pharmaceutically effective dose" indicates the amount enough to inhibit the vascular permeability with an applicable, reasonable or risky concentration. The dose can be determined by considering many factors such as the type of disease, severity of the disease, age, gender, activity of the drug, sensitivity to the drug, administration frequency and pathway, excretion, term of treatment, co-treatment drug and other factors regarded as relevant in the medicinal field. The composition of the present invention can be co-treated with other drugs or treated alone as an individual agent. For example, the composition of the present invention can be serially administered stepwise with the conventional treatment agents. Single-dose or multiple-dose administration is also possible. It is important to administer a most effective dose at a least amount without side effects with considering all the factors above, which can be determined by those in the art.

The present invention also relates to a method for regulating the vascular permeability comprising the step of regulating the expression of SCF or the receptor thereof.

Particularly, the said method is to suppress the vascular permeability by inhibiting SCF or the receptor thereof. This method is not only to down-regulate SCF or C-Kit (CD117), the SCF receptor, but also to reduce the phosphorylation thereof, and to inhibit the phosphorylation of eNOS (endothelial nitric oxide synthase) as well.

In this invention, the term "eNOS (endothelial nitric oxide synthase)" is an enzyme that stimulates the generation of endothelial NO (nitric oxide). When SCF was treated to the vascular endothelial cells in this invention, the intracellular transmitter Akt was phosphorylated and so was eNOS. The activated Akt-eNOS promoted the NO generation in the vascular endothelial cells, resulting in the increase of the vascular permeability.

The composition of the present invention could inhibit the phosphorylation of eNOS and accordingly inhibited the NO synthesis, resulting in the decrease of vascular permeability with suggesting that it could be effectively used for the treatment of vascular permeability related diseases.

Figure 2:
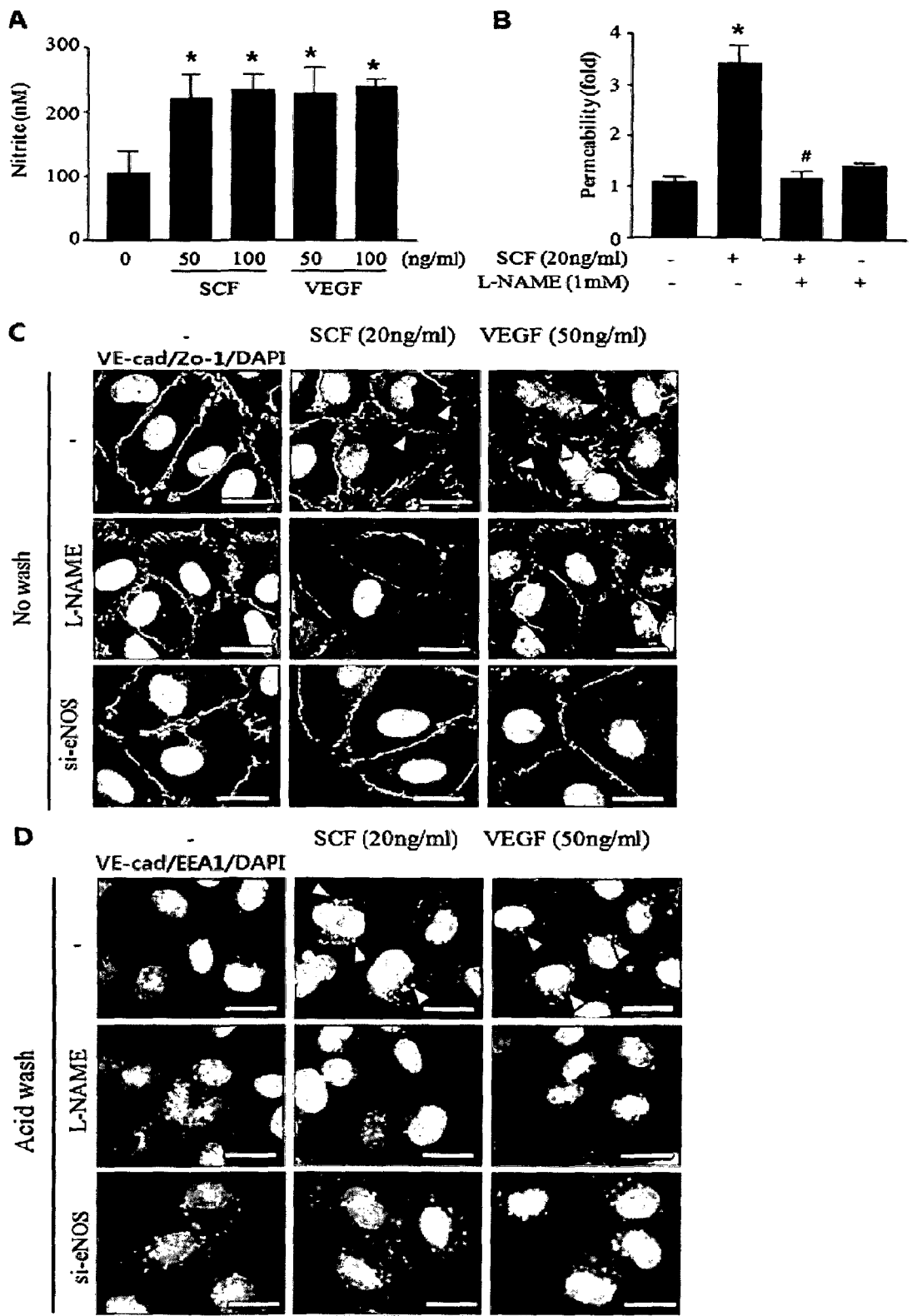
FIG. 2 illustrates the inducement of NO generation accomplished via AKT-eNOS, the intracellular signal transmitter, and endocytosis of VE-cadherin, the intercellular adherent protein, located on the surface of vascular endothelial cell by SCF.

In a preferred embodiment of the present invention, 20 ng of SCF was treated to the vascular endothelial cells introduced with the control siRNA and C-kit siRNA respectively to investigate the C-Kit dependent permeability of the vascular endothelial cells mediated by SCF. As a result, SCF increased the permeability of the vascular endothelial cells, which was more significant when the C-Kit expression was reduced thereby (FIG. 1B). After treating the vascular endothelial cells with SCF, phosphorylation of the intracellular transmitter Akt-eNOS was measured. As a result, SCF induced the phosphorylation and activation of Akt-eNOS and the activated enzyme increased the synthesis of NO in the vascular endothelial cells (FIG. 1C). When the NO synthesis was increased in the vascular endothelial cells, the vascular permeability was also increased (FIG. 2A). Such increase of the permeability, however, was down-regulated when L-NAME, the NO synthesis inhibitor, was treated thereto (FIG. 2B).

The said composition is a composition comprising a material inhibiting SCF or the receptor thereof. As explained hereinbefore, the material is not limited to a specific one if only the material has the effect of reducing the vascular permeability and can inhibit the expression or phosphorylation of SCF or the receptor thereof, for example C-Kit.

The present invention also relates to a method for screening an agent for treating vascular permeability related diseases comprising the following steps: (a) treating a sample from a patient suspected of having a disease associated with the vascular permeability with a candidate material; and (b) comparing the expression level of SCF or C-Kit, the SCF receptor, with that of the control group. The step (b) can further comprises the step of comparing the phosphorylation level of C-Kit, the SCF receptor, with that of the control group.

In this invention, the term "sample" can be whole blood, serum, blood, plasma, saliva, urine, sputum, lymph, cerebrospinal fluid, and intercellular fluid obtained from a patient suspected of having a vascular permeability related diseases. In addition, any sample containing cells suitable for the detection of the vascular permeability can be included without limitation.

In this invention, the term "control" can be whole blood, serum, blood, plasma, saliva, urine, sputum, lymph, cerebrospinal fluid, and intercellular fluid obtained from a normal subject showing the normal level of the vascular permeability, which is characterized by lower expression or phosphorylation level of SCF or C-Kit, the SCF receptor, than that of the experimental group suspected of having vascular permeability related diseases.

In this invention, the term "candidate material" indicates a test drug for measuring the expression or phosphorylation of SCF or C-Kit. Particularly, the candidate drug is tested to confirm if it can be used for the treatment of vascular permeability related diseases by regulating directly or indirectly the expression of SCF or C-Kit. For example, any random molecule or protein, oligopeptide, small organic molecule, polysaccharides, polynucleotide, and general compounds are included in the criteria of the "candidate material". This material can be either natural or synthetic.

In this invention, the term "agent for treating vascular permeability related diseases" indicates a substance or a mechanism that is functioning to reduce the vascular permeability.

The method for screening an agent for treating vascular permeability related diseases and for confirming the increase of the vascular permeability comprises the following steps: treating a material that can inhibit the vascular permeability to the control and the experimental groups; comparing the expression of SCF or C-Kit, the SCF receptor, with that of the control group; and determining the material as the material for treating vascular permeability related diseases when it is confirmed to reduce the expression of SCF or C-Kit, the SCF receptor, to the normal level of control group. The method for screening an agent for treating vascular permeability related diseases can also include the step of determining the material as the material for treating vascular permeability related diseases when it is confirmed to reduce the phosphorylation of SCF or C-Kit, the SCF receptor, to the normal level of control group. Therefore, observing the change of phosphorylation or expression of C-Kit and Akt-eNOS related signaling pathway is important to judge the qualification of the material.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Analysis of Vascular Endothelial Cell Permeability with Stem Cell Factor (SCF)

Vascular endothelial cells were loaded in the upper chamber of 12 well transwell filter (Corning Costar), followed by culture for 48 hours. The medium was replaced with the endothelical basal medium supplemented with 1% FBS, followed by further culture for 3 hours. SCF (R&D Systems, Minneapolis, Minn., USA) was treated thereto at different concentrations (10, 20, and 50 ng/ml) for 1 hour, followed by the treatment with FITC-conjugated dextran (fluorescein isothiocyanate-dextran) (1 mg/ml). 30 minutes later, the culture fluid was taken from the lower chamber, followed by the measurement with a fluorophotometer.

As a result, it was confirmed that the permeability of vascular endothelial cells was increased by the treatment of SCF dose-dependently (FIG. 1A).

Example 2

Analysis of C-Kit Dependent Permeability of Vascular Endothelial Cells with SCF

Vascular endothelial cells were loaded in 60 mm plate. The control siRNA 5'-AAUGGAAGACCACUCCCACUC-3' (SEQ. ID. NO: 1) and the C-Kit siRNAs 5'-UCAUUC-UUGAUGUCUCUGG-3' (SEQ. ID. NO: 2); 5'-UUUGAGUUCAGACAUGAGG-3' (SEQ. ID. NO: 3); 5'-UCUUAUAAAGUGCAGCUUC-3' (SEQ. ID. NO: 4); and 5'-UACAAUGCCAUUCUGAAGC-3' (SEQ. ID. NO: 5) were introduced in the cells by using lipofectamin. 24 hours later, the endothelial cells were transferred into the upper chamber of 12 well transwell filter (Corning Costar), followed by culture for 24 hours. The medium was replaced with the endothelical basal medium supplemented with 1% FBS, followed by further culture for 3 hours. SCF was treated thereto at the concentration of 20 ng/ml, followed by the treatment with FITC-conjugated dextran (1 mg/ml). 30 minutes later, the culture fluid was taken from the lower chamber, followed by the measurement with a fluorophotometer.

As a result, it was confirmed that the permeability of the endothelial cells was increased by SCF and this phenomenon was reduced significantly when the expression of C-Kit, the SCF receptor, was inhibited (FIG. 1B).

Example 3

Analysis of Intracellular Signaling Pathway of Vascular Endothelial Cells with SCF Vascular endothelial cells were loaded in 60 mm plate, followed by culture for 24 hours. The medium was replaced with the endothelical basal medium supplemented with 1% FBS, followed by further culture for 6 hours. SCF (20 ng/ml) was treated thereto and the cells were harvested over the time, followed by Western blotting.

As a result, it was confirmed that SCF induced the phosphorylation of C-Kit and Akt-eNOS, the signal transmitters of endothelial cells (FIG. 1C).

Example 4

Generation of NO (Nitric Oxide) in Vascular Endothelial Cells Induced by SCF

Vascular endothelial cells were cultured in 12 well plate for 24 hours. The medium was replaced with the endothelial basal medium supplemented with 1% FBS, which was then treated with SCF (20 ng/ml). The culture fluid was collected over the time, followed by centrifugation. The level of NO (nitric oxide) in the supernatant was measured (Total No/Nitrite/Nitrate Assay Kit).

As a result, it was confirmed that the level of NO was increased by SCF (FIG. 2A).

Example 5

Analysis of eNOS Dependent Increase of Vascular Endothelial Cell Permeability by SCF Vascular endothelial cells were loaded in the upper chamber of 12 well transwell filter (Corning Costar), followed by culture for 48 hours. The medium was replaced with the endothelical basal medium supplemented with 1% FBS, followed by further culture for 3 hours. L-NAME, the eNOS inhibitor, was pretreated (1 mM) to the cells for 30 minutes and then SCF (R&D Systems, Minneapolis, Minn., USA) was treated (20 ng/ml) thereto for 1 hour. FITC-conjugated dextran (fluorescein isothiocyanate-dextran) was also treated (1 mg/ml) thereto. 30 minutes later, the culture fluid was taken from the lower chamber, followed by the measurement with a fluorophotometer.

As a result, it was confirmed that the permeability of endothelial cells was increased by SCF and this increase was suppressed significantly by the eNOS inhibitor L-NAME (FIG. 2B).

Example 6

Analysis of VE-Cadherin Endocytosis of Vascular Endothelial Cell Induced by SCF

Vascular endothelial cells were cultured in 8 well chamber slide (Lab-Tek) for 48 hours. The medium was replaced with the endothelical basal medium supplemented with 1% FBS, followed by culture for 16 hours. The cells were treated with VE-cadherin antibody (R&D Systems, Minneapolis, Minn., USA) at 4° C. for 1 hour. SCF (20 ng/ml) and VEGF (50 ng/ml) (R&D Systems, Minneapolis, Minn., USA) were added thereto at 37° C. for 30 minutes to introduce VE-cadherin into the cells. To observe VE-cadherin on the cell surface, fixation was performed with 4% PFA, followed by immunostaining. To observe VE-cadherin in the inside of the cells migrated by SCF and VEGF mediated endocytosis, VE-cadherin on the cell surface was first removed by using an acid buffer (pH 2.7) and then the cells were fixed with 4% PFA, followed by immunostaining. Then, observation under a fluorescence microscope was performed.

As a result, it was confirmed that the expression of VE-cadherin on the cell surface, which is important for the cell-cell interaction of the vascular endothelial cells was reduced and endocytosis was induced instead by SCF (FIG. 2C and FIG. 2D).

Example 7

Analysis of eNOS Dependent VE-Cadherin Endocytosis of Vascular Endothelial Cells Induced by SCF The eNOS siRNAs 5'-ACCGGAACAGCA-CAAGAGUUAU-3' (SEQ. ID. NO: 6); 5'-AGCUG-CAAGGAUUCAGCAUUAU-3' (SEQ. ID. NO: 7); 5'-ACGGAACAGCACAAGAGUUAUA-3' (SEQ. ID. NO: 8); and 5'-CCAGGAGUAUCUUACCUGUAAA-3' (SEQ. ID. NO: 9) were introduced in vascular endothelial cells by using amaxa 4D nucleofector. 24 hours later, the cells were transferred in 8 well chamber slide (Lab-Tek), followed by culture for 24 hours. The medium was replaced with the endothelical basal medium supplemented with 1% FBS, followed by further culture for 16 hours. The cells were reacted with the VE-cadherin antibody at 4° C. for 1 hour. L-NAME was pretreated (1 mM) to the cells for 30 minutes and then SCF (20 ng/ml) and VEGF (50 ng/ml) were added thereto at 37° C. for 30 minutes to introduce VE-cadherin into the cells. To observe VE-cadherin on the cell surface, fixation was performed with 4% PFA, followed by immunostaining. To observe VE-cadherin in the inside of the cells migrated by SCF and VEGF mediated endocytosis, VE-cadherin on the cell surface was first removed by using an acid buffer (pH 2.7) and then the cells were fixed with 4% PFA, followed by immunostaining. Then, observation under a fluorescence microscope was performed.

As a result, it was confirmed that endocytosis of VE-cadherin, induced by SCF, was inhibited by the suppression of eNOS expression and by the eNOS inhibitor but the expression of VE-cadherin on the cell surface was maintained (FIG. 2C and FIG. 2D).

Example 8

Analysis of Vascular Permeability Increase Induced by SCF in a Mouse Model

Evans blue dye 100 was injected intravenously in the tail of C57/BL mouse. 10 minutes later, SCF and SCF receptor inhibiting antibody (anti-cKit IgG: Monoclonal anti-SCF receptor neutralization antibody: R&D Systems, Minneapolis, Minn., USA) were injected intradermally on the back of the mouse. 20 minutes later, the back skin of the mouse was collected. The region where Evans blue dye was penetrated through tissues was photographed. The skin was fixed in formamide, which stood at room temperature for 4 days. Then, $OD_{620}$ was measured by using a spectrophotometer.

As a result, it was confirmed that the vascular permeability of the mouse was increased (FIG. 3A and FIG. 3B), and this increase was significantly reduced by the SCF receptor inhibiting antibody (FIG. 3C and FIG. 3D).

Example 9

Angiography to Measure SCF Mediated Vascular Permeability with Mouse Retinal Vessels SCF and SCF receptor inhibiting antibody were injected in the retina of C57/BL6 mouse. 24 hours later, the mouse was anesthetized and then intracardiac FITC-dextran injection was performed in order to let the fluorescein flow through blood. 30 minutes later, the retina of the mouse was extracted and observed under a fluorescence microscope after flat mounting.

As a result, it was confirmed that the fluorescein was released around the retinal vessels, suggesting that the retinal vessel permeability was increased in the mouse injected with SCF (FIG. 4A and FIG. 4B). This increase of the permeability was significantly reduced by the treatment of SCF receptor inhibiting antibody (FIG. 4C and FIG. 4D).

Example 10

Increase of SCF Expression in Diabetic Retinopathy Animal Model 150 mg/kg of STZ (streptozotocin, Sigma) was injected intraperitoneally in SD (Sprague Dawley) rat. 3 days later, the blood sugar level was measured. The animals demonstrating 250 mg/dL or higher blood sugar level were separated and diabetic retinopathy was induced. The retinas of those SD rats were extracted one week and 4 weeks after the inducement of diabetic retinopathy. RNA was isolated therefrom by using Trizol reagent (Invitrogen). Then, real time PCR was performed to investigate the expressions of SCF and VEGF.

As a result, it was confirmed that the expressions of SCF and VEGF were increased over the time in the rat induced with diabetic retinopathy (FIG. 5A and FIG. 5B), suggesting that SCF was an important factor to cause diabetic retinopathy, one of the vascular permeability related diseases.

Example 11

Increase of Vascular Permeability in Diabetic Retinopathy Animal Model and Decrease Thereof by SCF Inhibiting Antibody SCF inhibiting antibody (anti-SCF IgG: Monoclonal anti-SCF neutralization antibody: R&D Systems, Minneapolis, Minn., USA) was injected in the retina of a rat induced with diabetic retinopathy in Example 10. 2 weeks later, intracardiac FITC-dextran injection was performed in the heart of the anesthetized rat to let the fluorescein flow through blood. 30 minutes later, the retina of the rat was extracted and observed under a fluorescence microscope after flat mounting.

As a result, it was confirmed that the fluorescein was released around the retinal vessels, suggesting that the retinal vessel permeability was increased in the rat induced with diabetic retinopathy by the injection of STZ. This increase of permeability was significantly reduced by the treatment of SCF inhibiting antibody (anti-SCF IgG) (FIG. 6), suggesting that the anti-SCF IgG was effective in treating diabetic retinopathy.

The above results confirmed that SCF of the present invention could be used as a regulator that could increase vascular permeability, and thus a material that could inhibit SCF or C-Kit, the SCF receptor, could be effectively used for the treatment and prevention of vascular permeability related diseases.

The invention claimed is:

1. A method for treating or preventing vascular permeability related diseases comprising the steps of selecting a patient in need of treating or preventing vascular permeability related diseases, and administering a composition comprising a material for inhibiting SCF (stem cell factor) or the receptor thereof to the patient, wherein the vascular permeability related diseases is selected from the group consisting of
non-proliferative diabetic retinopathy,
ROP (retinopathy of prematurity),
age-related macular degeneration,
corneal dystrophy,
retinoschises,
Stargardt's disease,
autosomal dominant druzen,
Best's macular dystrophy,
cystoid macular edema,
ischemic retinopathy,
inflammation-induced retinal degenerative disease,
X-linked juvenile retinoschisis,
Malattia Leventinese (ML),
Doyne honeycomb retinal dystrophy, and
vascular endothelial cell related inflammatory disease.

2. The method for treating or preventing vascular permeability related diseases according to claim 1, wherein the SCF receptor is C-Kit.

3. The method for treating or preventing vascular permeability related diseases according to claim 1, wherein the material inhibiting SCF or the receptor thereof is selected from the group consisting of siRNA, an antisense oligonucleotide, an aptamer, and an antibody specific to the SCF or the receptor thereof.

4. The method for treating or preventing vascular permeability related diseases according to claim 3, wherein the material inhibiting the SCF receptor is C-Kit siRNA or SCF receptor inhibiting antibody.

5. The method for treating or preventing vascular permeability related diseases according to claim 4, wherein the C-Kit siRNA has the nucleotide sequence of SEQ ID NO:2, 3, 4, or 5.

6. The method for treating or preventing vascular permeability related diseases according to claim 1, wherein the treatment of vascular permeability related diseases is performed by inhibiting the permeability of vascular endothelial cells.

7. A method for regulating vascular permeability comprising the steps of selecting a patient in need of regulating vascular permeability related diseases, and regulating the expression of SCF or the receptor thereof in vivo in the patient by using a composition comprising a material for inhibiting SCF or the receptor thereof, wherein the vascular permeability related diseases is selected from the group consisting of
non-proliferative diabetic retinopathy,
ROP (retinopathy of prematurity),
age-related macular degeneration,
corneal dystrophy,
retinoschises,
Stargardt's disease,
autosomal dominant druzen,
Best's macular dystrophy,
cystoid macular edema,
ischemic retinopathy,
inflammation-induced retinal degenerative disease,
X-linked juvenile retinoschisis,
Malattia Leventinese (ML),
Doyne honeycomb retinal dystrophy, and
vascular endothelial cell related inflammatory disease.

8. A method for screening an agent for treating vascular permeability related diseases comprising the following steps: (a) treating a sample from a patient suspected of having vascular permeability related diseases with a candidate material; (b) comparing the expression level of SCF or the receptor thereof with that of the untreated control group, and (c) identifying a candidate material showing decreased expression level of SCF or the receptor thereof as an agent for treating vascular permeability related diseases.

9. The method for screening an agent for treating vascular permeability related diseases according to claim 8, wherein the SCF receptor is C-Kit.

10. The method for screening an agent for treating vascular permeability related diseases according to claim 9, wherein the step (b) further comprises the step of comparing the phosphorylation of C-Kit with that of the control group.

* * * * *